United States Patent [19]
Hirota

[11] Patent Number: 5,961,489
[45] Date of Patent: Oct. 5, 1999

[54] SPRAY ADAPTORS FOR SPRAYING COLLUNARIUM AND SPRAYERS EMPLOYING THE SPRAY ADAPTORS

[75] Inventor: Koji Hirota, Kanazawa, Japan

[73] Assignee: Shinko Kagaku Kabushiki Kaisha, Ishikawa-ken, Japan

[21] Appl. No.: 09/037,387

[22] Filed: Mar. 10, 1998

[30] Foreign Application Priority Data

Oct. 8, 1997 [JP] Japan ................................. 9-276207

[51] Int. Cl.⁶ .................................................. A61M 5/00
[52] U.S. Cl. ........................................................... 604/94
[58] Field of Search ............................ 604/94, 239, 237

[56] References Cited

U.S. PATENT DOCUMENTS

| | | | |
|---|---|---|---|
| 3,066,669 | 12/1962 | De Melfy | 604/94 |
| 3,502,078 | 3/1970 | Hill et al. | 604/94 |
| 3,874,380 | 4/1975 | Baum | 604/94 |

*Primary Examiner*—John D. Yasko
*Attorney, Agent, or Firm*—Jordan and Hamburg

[57] ABSTRACT

A spray adaptor includes a main adaptor element having a pair of spray nozzles and a connector attached to the main adaptor element. A sprayer for spraying collunarium is prepared by fitting the connector of the spray adaptor to an outlet of a syringe. The collunarium discharged from the syringe is guided to the spray nozzles and sprayed into both nostrils at one time.

6 Claims, 10 Drawing Sheets

SPRAY ADAPTORS FOR SPRAYING COLLUNARIUM AND SPRAYERS EMPLOYING THE SPRAY ADAPTORS

BACKGROUND OF THE INVENTION

The present invention relates to spray adaptors which make it possible to spray collunarium into both nostrils at one time as well as to sprayers employing such spray adaptors.

A dedicated spraying device is often used for applying collunarium to nasal mucous membranes in the back of the nasal cavity. Examples of such devices are disclosed in Japanese Unexamined Patent Publications Nos. 8-47530 and 6-70980.

A conventionally known construction of a spraying device is such that a spray chip is attached to or built in an extreme end portion of a hand-operated syringe, the extreme end portion of the syringe being formed into a generally cylindrical shape suitable for insertion into a human nostril. The extreme end portion of the syringe which is loaded with collunarium is inserted into one of the nostrils, and the syringe is operated to spray the collunarium through the chip onto the nasal mucous membranes. In this construction, the collunarium is usually applied through each of the nostrils.

A chronic problem of the spraying devices of the prior art is that their operation is time-consuming and awkward. This is because the collunarium should be applied through one nostril after the other of a patient as the conventional spraying devices lack the ability to spray the collunarium into both nostrils at the same time.

SUMMARY OF THE INVENTION

It is an object of the present invention to provide a spray adaptor and sprayer which have overcome the problems residing in the prior art.

According to an aspect of the present invention, a spray adaptor for spraying collunarium comprises: a connector adapted to be fitted to and removed from a liquid outlet of a syringe; and a main adaptor element joined to the connector. The main adaptor element has a pair of spray nozzles suitably formed for simultaneous insertion into both nostrils.

According to another aspect of the present invention, a sprayer for spraying collunarium comprises a syringe and a spray adaptor mounted to said syringe. The spray adaptor includes: a connector detachably fitted to a liquid outlet of the syringe; and a main adaptor element joined to the connector. The main adaptor element has a pair of spray nozzles suitably formed for simultaneous insertion into both nostrils.

These and other objects, features and advantages of the invention will be more readily understood from the following detailed description when read in conjunction with the appended drawings.

DETAILED DESCRIPTION OF THE PREFERRED EMBODIMENTS OF THE INVENTION

Specific embodiments of the invention will now be described, by way of example, with reference to the accompanying drawings.

Figure 1:
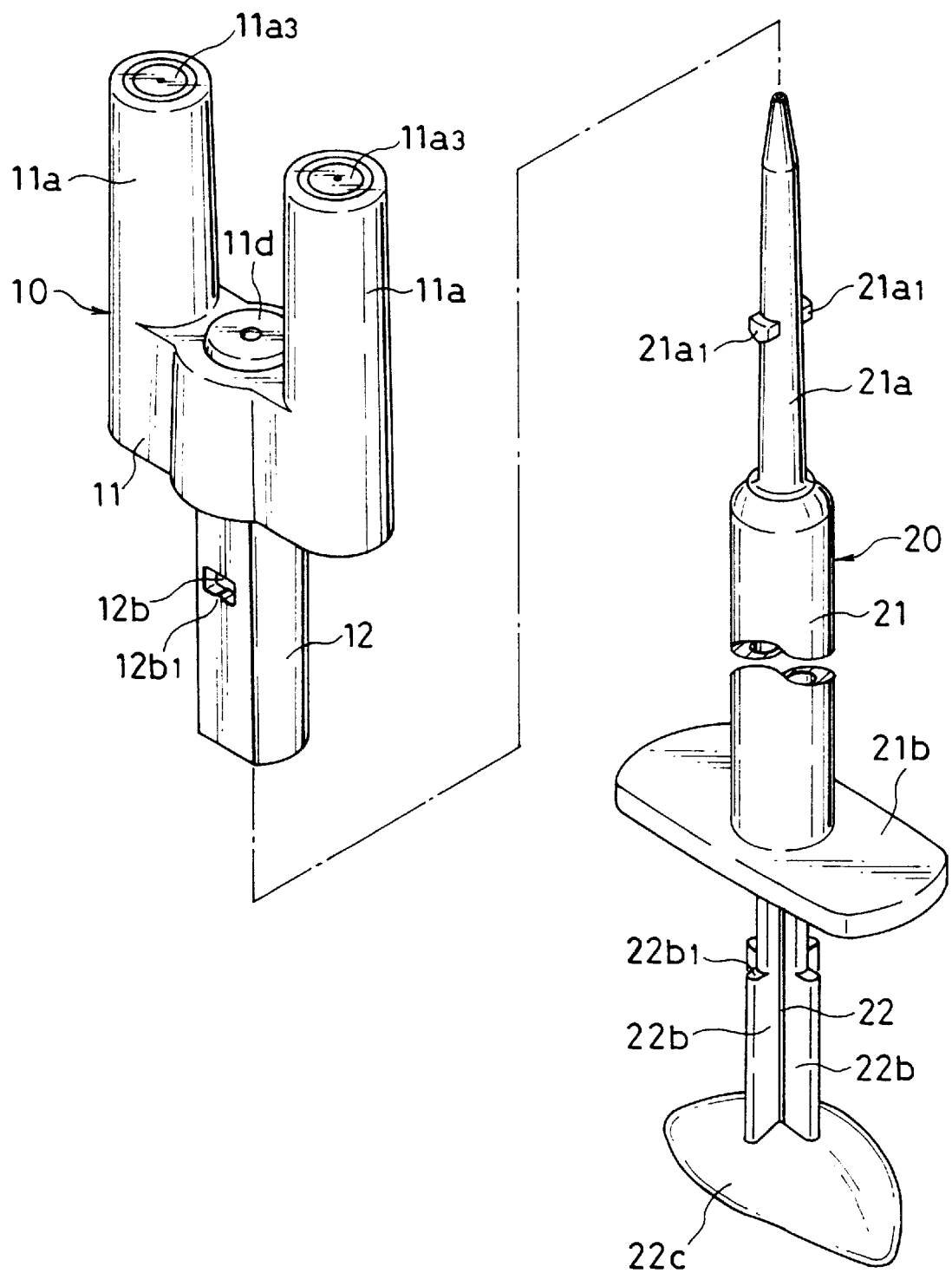
FIG. 1 is an exploded perspective view of a spray adaptor fitted with a connector and a syringe according to a preferred embodiment of the invention.
Figure 2:
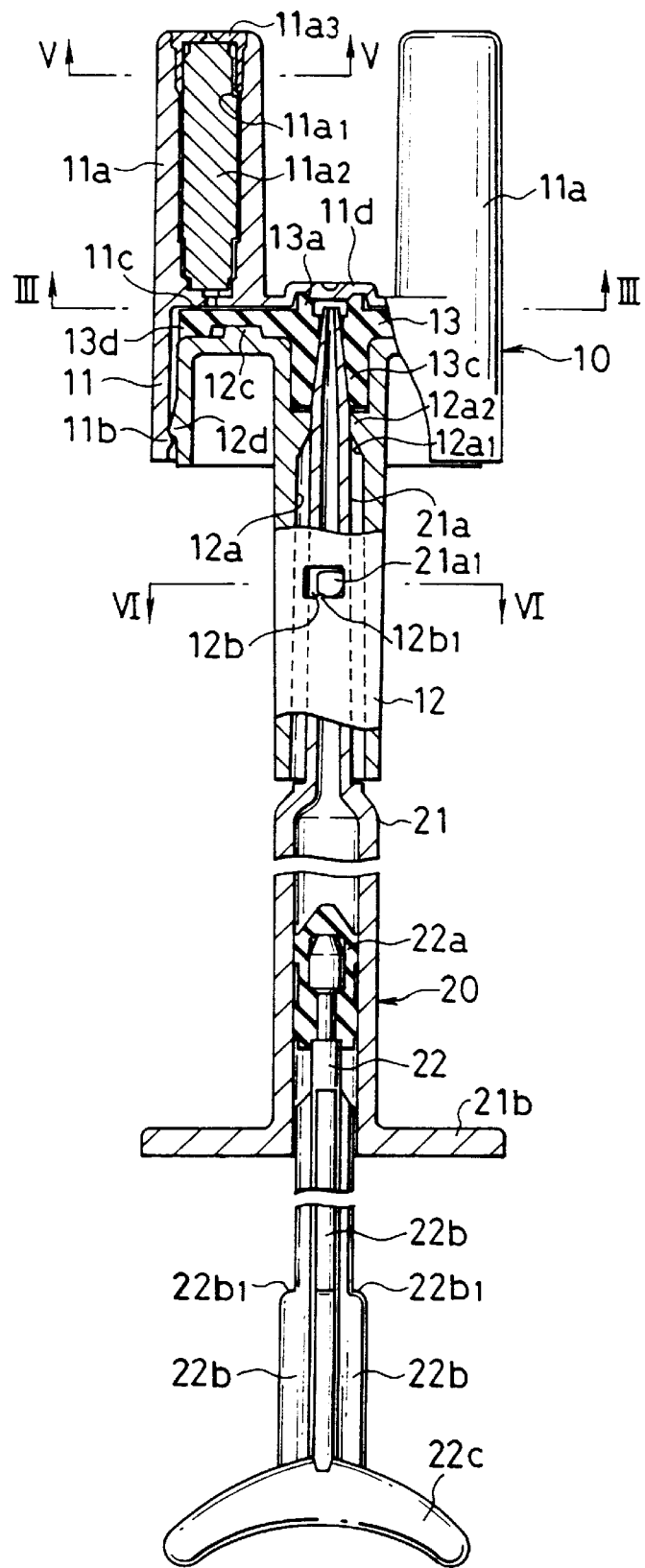
FIG. 2 is a vertical sectional view of a sprayer of the invention.

Referring to FIGS. 1 and 2, a spray adaptor 10 for spraying collunarium comprises a main adaptor element 11 and a connector 12 which is fitted into the main adaptor element 11. This spray adaptor 10 is assembled with a syringe 20 to form a collunarium sprayer.

Figure 3:
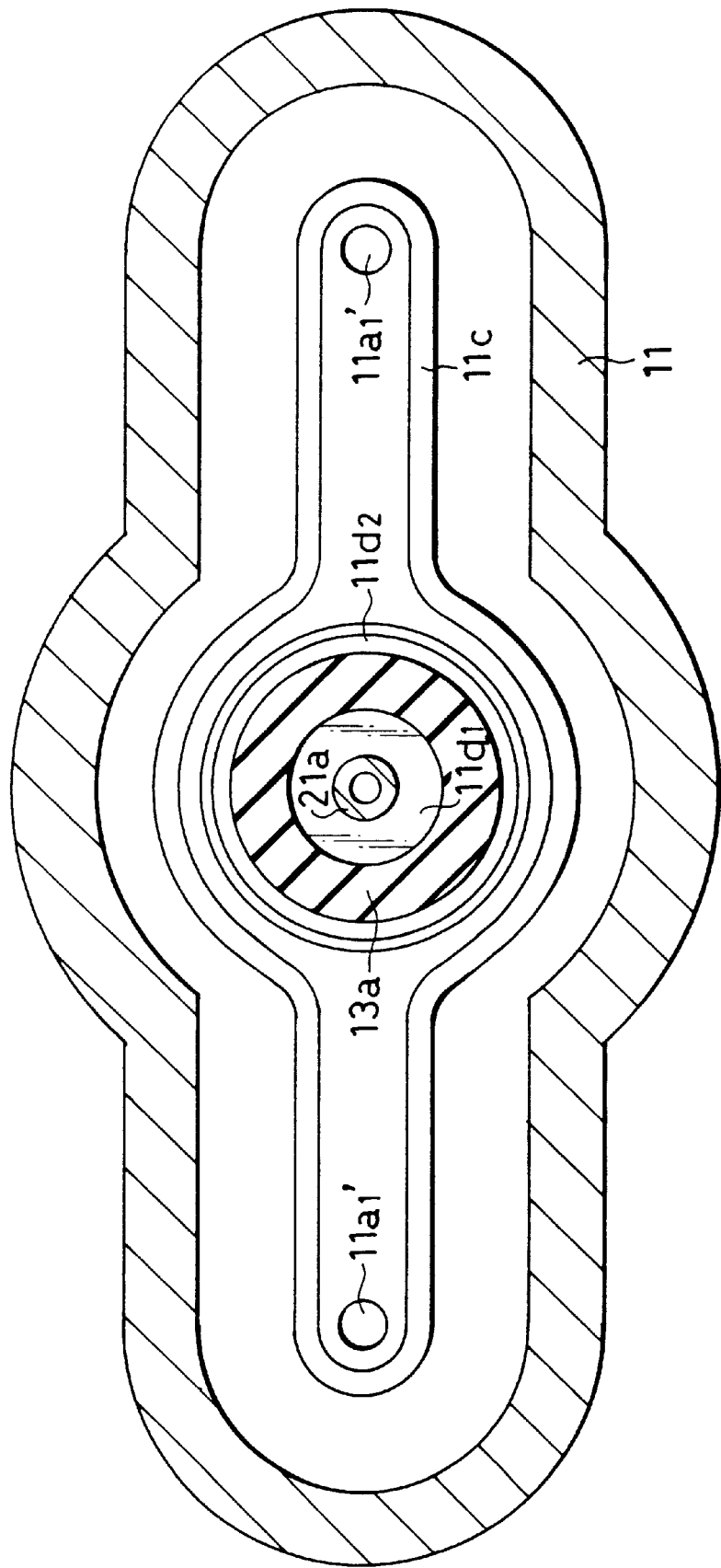
FIG. 3 is an enlarged horizontal sectional view taken along lines III—III of FIG. 2.

The main adaptor element 11 has a skirt-like base portion having parallel side faces, generally elliptical shape in horizontal cross-section with its middle part bulging both frontward and rearward in circular arc form (FIG. 3). Formed at upper-right and upper-left parts of the base portion of the main adaptor element 11 are a pair of upward-directed parallel spray nozzles 11a, each having a generally cylindrical shape slightly tapered off upward. There are formed snap-on ribs 11b on the left and right sides of an inner surface of the base portion of the main adaptor element 11. As will be explained later in further detail, these snap-on ribs 11b retain the connector 12 in position when it is fitted into the spray adaptor 10. On the underside of a top plate of the base portion of the main adaptor element 11, there is formed a sealing rib 11c which has an inverted triangular shape in vertical section and runs in the manner of a downward-projecting ridge to form essentially the same shape (but reduced in size) as the horizontal cross-section of the base portion in plan view, as shown in FIGS. 2 and 3. As can be seen from FIGS. 3 and 4, a raised caplike portion 11d is formed on the top plate of the base portion of the main adaptor element 11 at the midpoint between the left and right spray nozzles 11a, and a ring-shaped groove $11d_2$ is made on a bottom surface of the caplike portion 11d with a low-profile circular projecting part $11d_1$ formed within the groove $11d_2$. The projecting part $11d_1$ is surrounded by a slanted peripheral surface.

Figure 5:
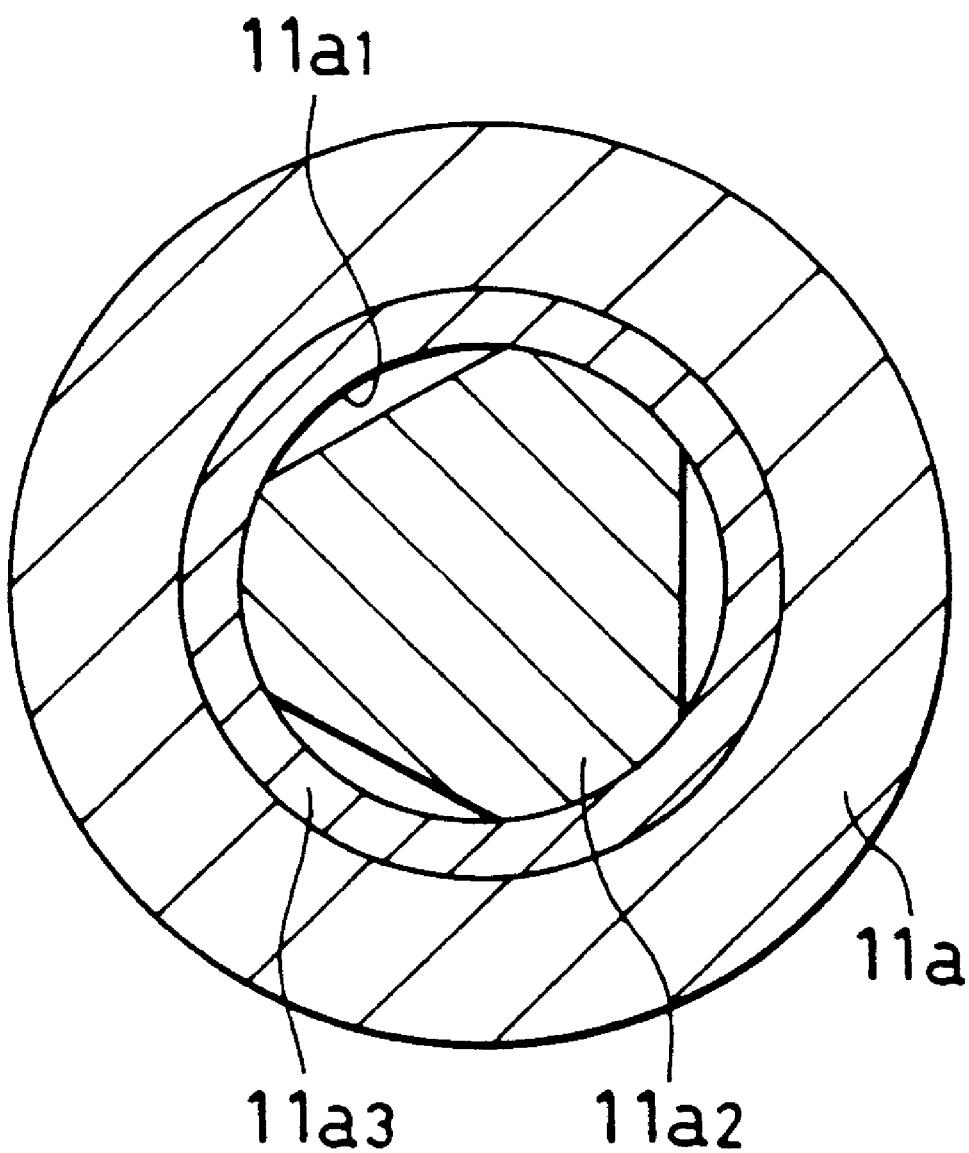
FIG. 5 is an enlarged vertical sectional view taken along lines V—V of FIG. 2.

Referring to FIGS. 2, 3 and 5, each spray nozzle 11a has a cylindrical hole $11a_1$ whose lower intake opening $11a_1'$ is located inside the sealing rib 11c, and a rodlike core member $11a_2$ having a plurality of flat side faces close to its upper and lower ends is fitted in the cylindrical hole $11a_1$. The core member $11a_2$ is aligned with the axis of the cylindrical hole $11a_1$ in a manner that a specified clearance is formed between the core member $11a_2$ and the cylindrical hole $11a_1$. Further, a nozzle chip $11a_3$ is fitted in the upper end of each spray nozzle 11a. In this construction, the cylindrical hole $11a_1$ of each spray nozzle 11a passes from the lower intake opening $11a_1'$ to the upper nozzle chip $11a3$ with the effective cross-sectional area of the cylindrical hole $11a_1$ reduced by insertion of the core member $11a_2$.

Figure 6A:
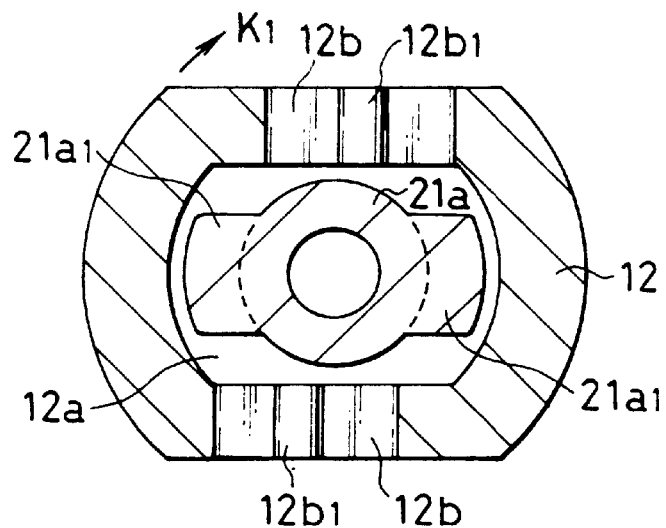
FIGS. 6A to 6C are diagrams illustrating how the syringe is fitted into the connector.
Figure 6B:
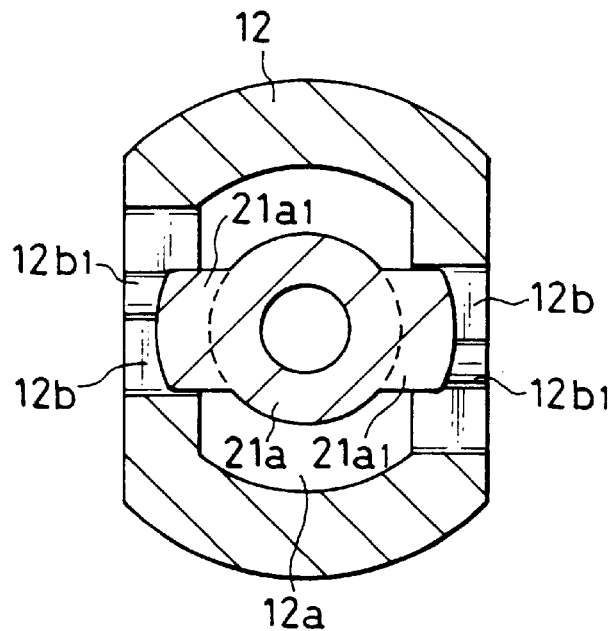
Figure 6C:
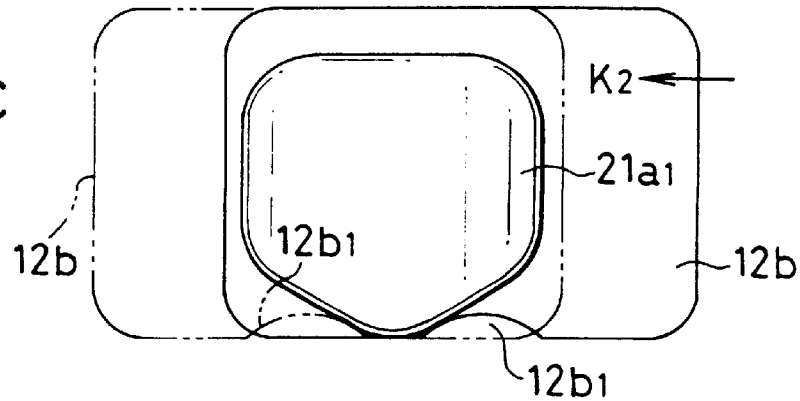

The connector 12 is fitted into a lower part of the main adaptor element 11 as depicted in FIGS. 2 and 6A–6C, in which FIG. 6B is an enlarged horizontal sectional view taken along lines VI—VI of FIG. 2; FIG. 6A is a diagram illustrating how the components shown in FIG. 6B are assembled; and FIG. 6C is a diagram illustrating how each locking projection $21a_1$ of a nozzle portion $21a$ of the syringe 20 becomes locked in a corresponding opening 12b formed in the connector 12.

The connector 12 is formed into a cylindrical shape with a nozzle insertion hole 12a having an oval-shaped cross section formed in its interior. An upper portion of the inner surface of the nozzle insertion hole 12a is shaped to form a stepped part $12a_2$ (refer to FIG. 2) associated with a downward-broadening conical guide surface $12a_1$. In approximately the middle of the vertical extension of the connector 12, there are formed a pair of openings 12b, one in front and one in back, which are horizontally offset from each other in the direction of the major axis of the oval-shaped cross section of the nozzle insertion hole 12a. As shown in FIG. 6C, a rounded hump $12b_1$ is formed on a lower side of each opening 12b. An upper portion of the connector 12 is shaped to fit the shape of the lower part of the main adaptor element 11. The connector 12 has on its top surface left and right projections 12c (refer to FIG. 2) which are used for positioning the connector 12. The connector 12 has a skirt-like structure at its top similar to the base portion of the main adaptor element 11, and a pair of snap-on ribs 12d which become interlocked with the snap-on ribs 11b of the main adaptor element 11 are formed on the left and right sides of an outside surface of the skirt-like structure. When the connector 12 is pushed into the main adaptor element 11, the snap-on ribs 12d of the connector 12 slip over and hook onto the snap-on ribs 11b of the main adaptor element 11. As a consequence, the connector 12 is securely mated with the main adaptor element 11 so that the main adaptor element 11 will not accidentally come off the connector 12.

Figure 4:
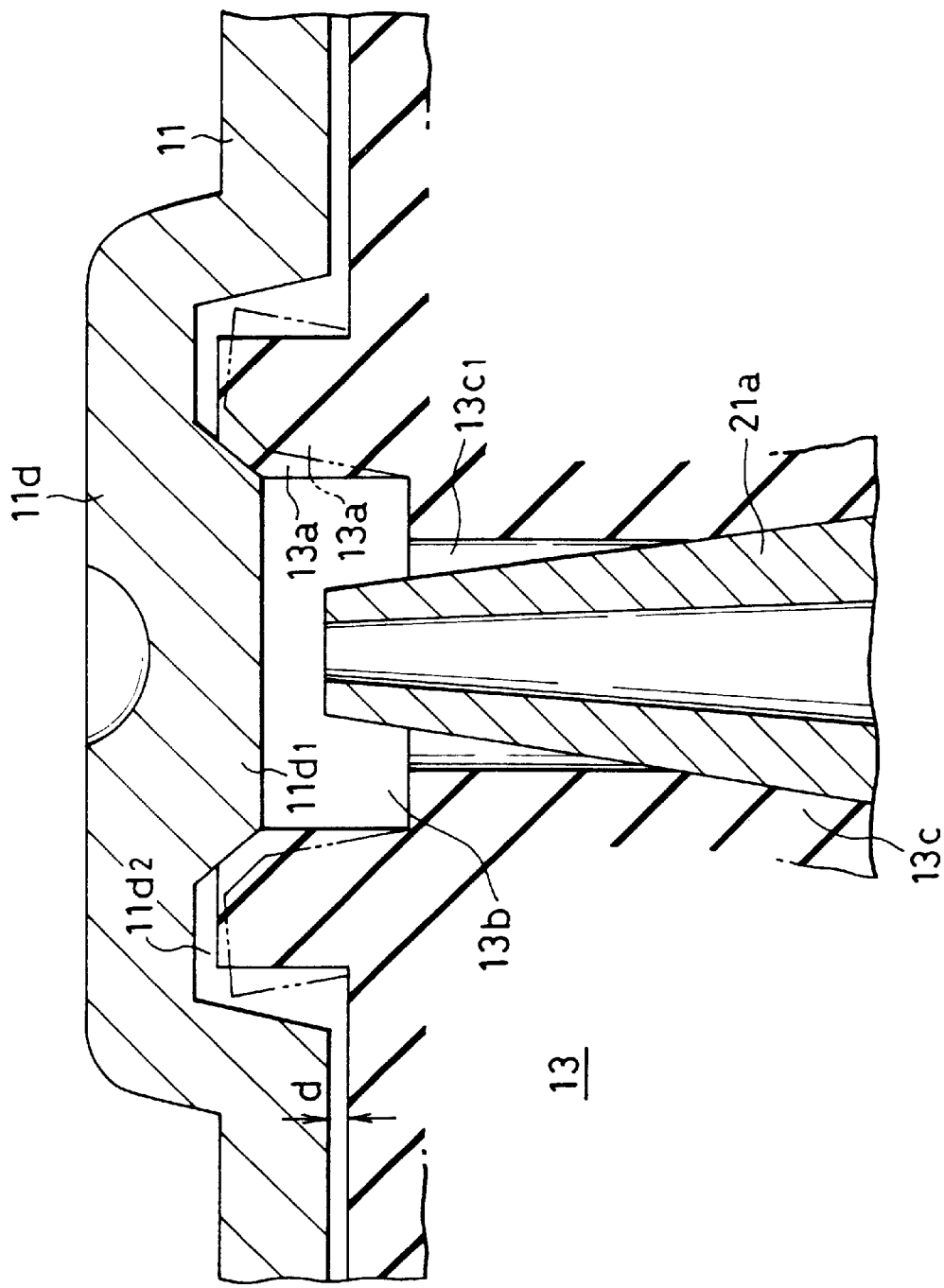
FIG. 4 is a partially enlarged view of FIG. 2.

As shown in FIGS. 2 and 4, a seal member 13 made of an elastic material is fitted between the main adaptor element 11 and the connector 12. The seal member 13 is formed into such a shape that will properly fit an upper inside surface of the base portion of the main adaptor element 11 and the top surface of the connector 12. In the middle of a top surface of the seal member 13, there is formed an annular projection 13a which comes into close contact with the slanted peripheral surface of the projecting part $11d_1$ of the main adaptor element 11. A space surrounded by the projection 13a forms a round chamber 13b. Further formed in the seal member 13 beneath the chamber 13b is a generally cylindrical receptacle 13c which is positioned above the nozzle insertion hole 12a of the connector 12 and accommodates the nozzle portion 21a of the syringe 20. A vertical through hole $13c_1$ passing through the receptacle 13c and connecting to the chamber 13b is made in the middle of the seal member 13. This through hole $13c_1$ has a cone-shaped inner surface as illustrated.

The seal member 13 has on its underside left and right recesses 13d (refer to FIG. 2) and is positioned on top of the connector 12 when its left and right projections 12c are fitted into the recesses 13d in the seal member 13. When the seal member 13 is properly positioned in this manner, the sealing rib 11c of the main adaptor element 11 provides a liquid-tight seal between the main adaptor element 11 and the connector 12. Sandwiched between the main adaptor element 11 and the connector 12, the seal member 13 is held in firm contact with the top surface of the connector 12 and the top plate of the base portion of the main adaptor element 11 on the outside of the sealing rib 11c. On the other hand, a clearance d is provided between the seal member 13 and the top plate of the base portion of the main adaptor element 11 on the inside of the sealing rib 11c as shown in FIG. 4, and this clearance d connects both the left and right intake openings $11a_1'$ (refer to FIG. 3) of the spray nozzles 11a to the ring-shaped groove $11d_2$ in the middle of the base portion of the main adaptor element 11.

The syringe 20 comprises a hollow barrel 21 and a plunger 22 which can be inserted into and removed from the hollow barrel 21 as shown in FIGS. 1 and 2. The nozzle portion 21a is an elongated tubular element having a cone-shaped tip portion and is provided at an upper end of the hollow barrel 21. Formed at a lower end of the hollow barrel 21 is an oval-shaped finger flange 21b which extends to both the left and right (as illustrated in FIG. 2). As shown in FIGS. 6A–6C, a pair of locking projections $21a_1$, each having a downward swollen part, are formed on opposite sides of the nozzle portion 21a in such a way that they fit into a corresponding pair of openings 12b formed in the connector 12.

The plunger 22 is reduced in diameter at its top end with an elastic piston 22a mounted on the top end so that the plunger 22 can slide up and down within the hollow barrel 21. The plunger 22 has a finger rest 22c at its bottom end and a plurality of radially arranged guide ribs 22b which extend upward from the finger rest 22c approximately halfway along the vertical extension of the plunger 22. Stepped upper ends $22b_1$ of these guide ribs 22b serve as a stopper for restricting upward excursion of the plunger 22.

The syringe 20 is assembled with the spray adaptor 10 by inserting the nozzle portion 21a of the syringe 20 all the way into the nozzle insertion hole 12a of the connector 12 and can be removed therefrom when necessary. As can be seen from FIGS. 2 and 4, the nozzle portion 21a is guided along the guide surface $12a_1$ of the nozzle insertion hole 12a when inserted therein. When the nozzle portion 21a is fully inserted, it passes through the vertical through hole $13c_1$ in the seal member 13 with its upper end opening located within the chamber 13b. The inner surface of the receptacle 13c comes into liquid-tight contact with a cone-shaped outer surface of the nozzle portion 21a, and elastic deformation of the receptacle 13c produces a downward-pushing force which acts on the nozzle portion 21a.

The syringe 20 is fitted to the connector 12 in the following fashion. First, the nozzle insertion hole 12a of the connector 12 is placed over the nozzle portion 21a of the hollow barrel 21 so that the direction of the major axis of the nozzle insertion hole 12a aligns with the direction of the pair of locking projections $21a_1$ as illustrated in FIG. 6A. The connector 12 is then turned about the nozzle portion 21a in the direction of arrow $K_1$ until the locking projections $21a_1$ properly lock in the openings 12b in the connector 12 as shown in FIG. 6B. More particularly, the two openings 12b move relative to the respective locking projections $21a_1$ in the direction of arrow $K_2$ shown in FIG. 6C when the connector 12 is turned. In this process, the rounded hump $12b_1$ formed in each opening 12b slips below the corresponding locking projection $21a_1$ as shown by an alternate long and two short dashed curved line in FIG. 6C. Since the nozzle portion 21a is forced downward by the elastic restoring force exerted by the receptacle 13c of the seal member 13, the rounded humps $12b_1$ in the openings 12b catch on the respective locking projections $21a_1$, where the connector 12 is firmly locked onto the nozzle portion 21a with minimal chances of accidental disconnection due to their relative rotation.

Figure 7:
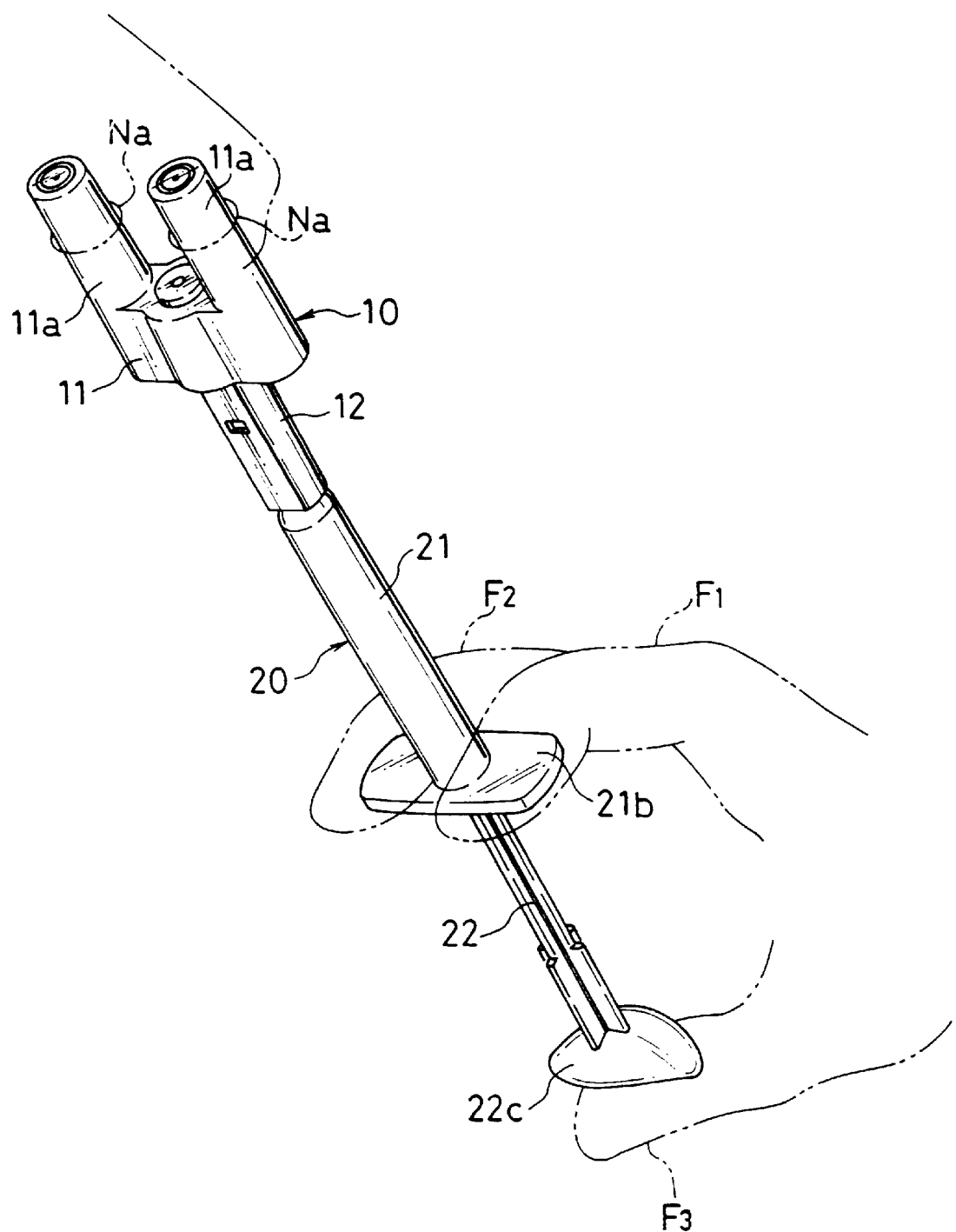
FIG. 7 is a diagram illustrating how the sprayer is operated.

The syringe 20 is loaded with collunarium before it is fitted with the spray adaptor 10. This is accomplished by inserting the nozzle portion 21a into a vial (not shown) containing the collunarium and pulling the plunger 22 fitted with the elastic piston 22a in the direction of the finger flange 21b to suck the collunarium. The spray adaptor 10 is attached to the syringe 20 thus loaded with the collunarium by forcing its nozzle portion 21a into the connector 12. Then, a user of the collunarium sprayer places his or her index finger $F_1$ and middle finger $F_2$ on the finger flange 21b and thumb $F_3$ on the finger rest 22c, inserts the spray nozzles 11a into both nostrils Na of a patient (inclusive of a user), and sprays the collunarium in the hollow barrel 21 into both nostrils Na at one time by pushing the plunger 22 of the syringe 20 as illustrated in FIG. 7.

The annular projection 13a of the seal member 13 remains in close contact with the slanted peripheral surface of the projecting part $11d_1$ of the main adaptor element 11 as shown by solid lines in FIG. 4 to prevent the collunarium from flowing into the cylindrical hole $11a_1$ of each spray nozzle 11a until the pressure of the collunarium introduced into the chamber 13b reaches a specified level. When the pressure of the collunarium within the chamber 13b reaches or exceeds the specified level, the annular projection 13a spreads out as shown by alternate long and two short dashed lines in FIG. 4 as a result of its elastic deformation, whereby the chamber 13b is connected to the cylindrical hole $11a_1$ of each spray nozzle 11a. It will be recognized from the above discussion that the annular projection 13a of the seal member 13 serves as an on-off valve which permits the collunarium supplied from the syringe 20 to flow into the individual cylindrical holes $11a_1$ at the specified pressure level and thereby regulates the pressure at which the collunarium is sprayed through the spray nozzles 11a.

The spray adaptor 10 is removed from the nostrils of the patient when a specified amount of the collunarium within the hollow barrel 21 has been fed into the spray adaptor 10 and sprayed into the nostrils by operating the plunger 22. The spray adaptor 10 may then be removed from the syringe 20 by turning the spray adaptor 10 about the nozzle portion 21a of the syringe 20 in a direction opposite to the arrow $K_1$ of FIG. 6A to release the locking projections $21a_1$ from the rounded hump s $12b_1$ of the respective openings 12b in the connector 12.

Figure 8:
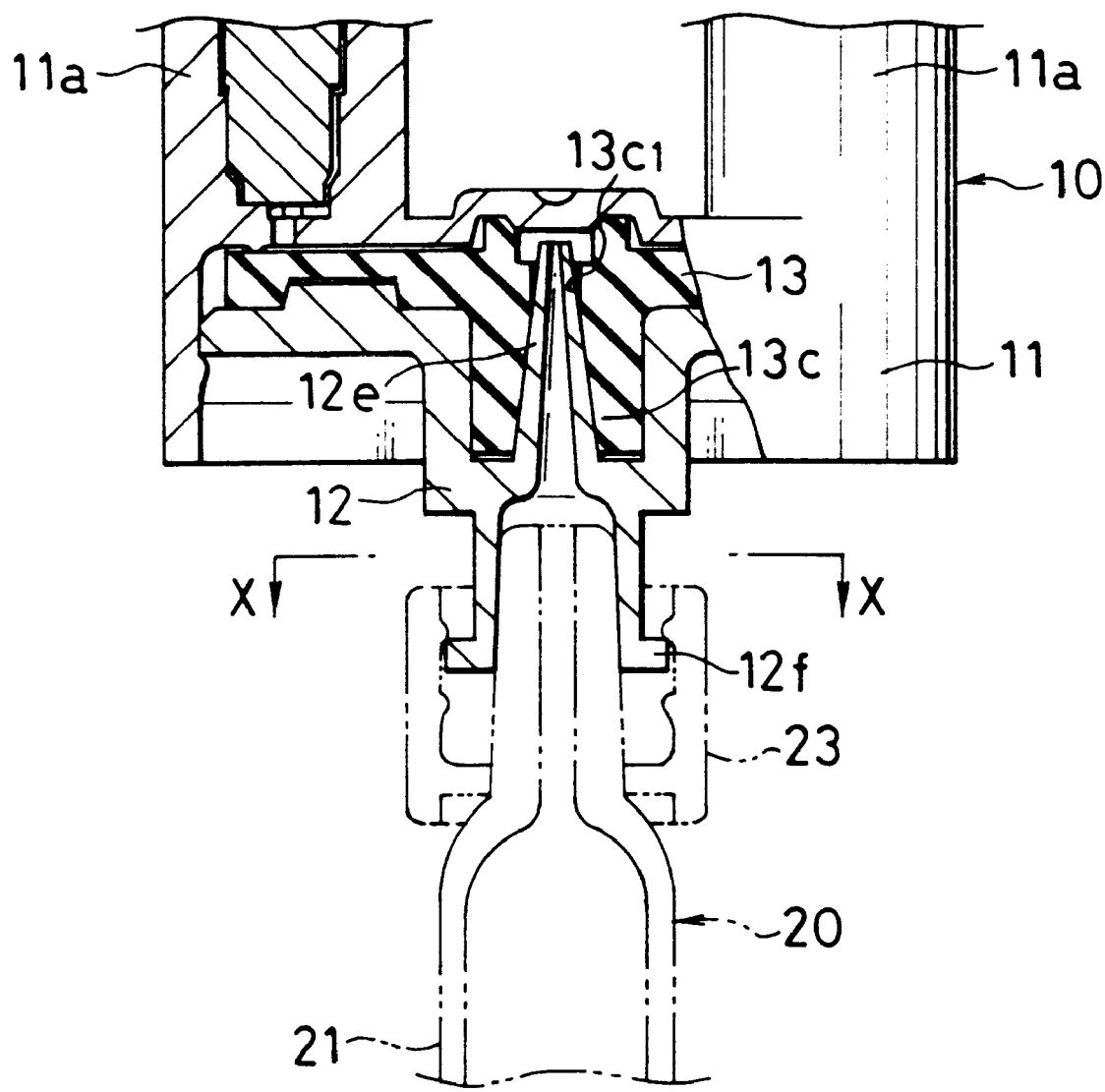
FIG. 8 is a fragmentary vertical sectional view illustrating one variation of the preferred embodiment.
Figure 9B:
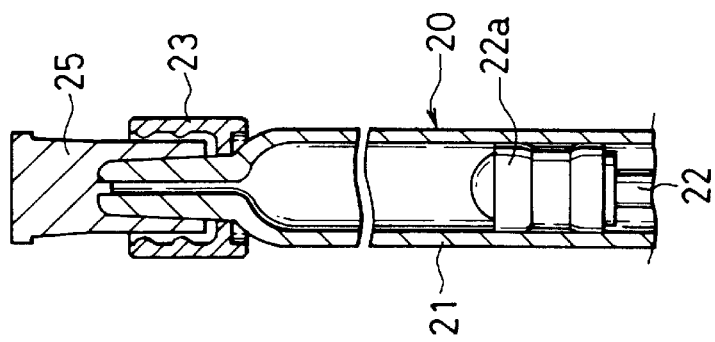
FIGS. 9A and 9B diagrams showing the construction of a syringe to be used in the variation of FIG. 8.
Figure 9A:
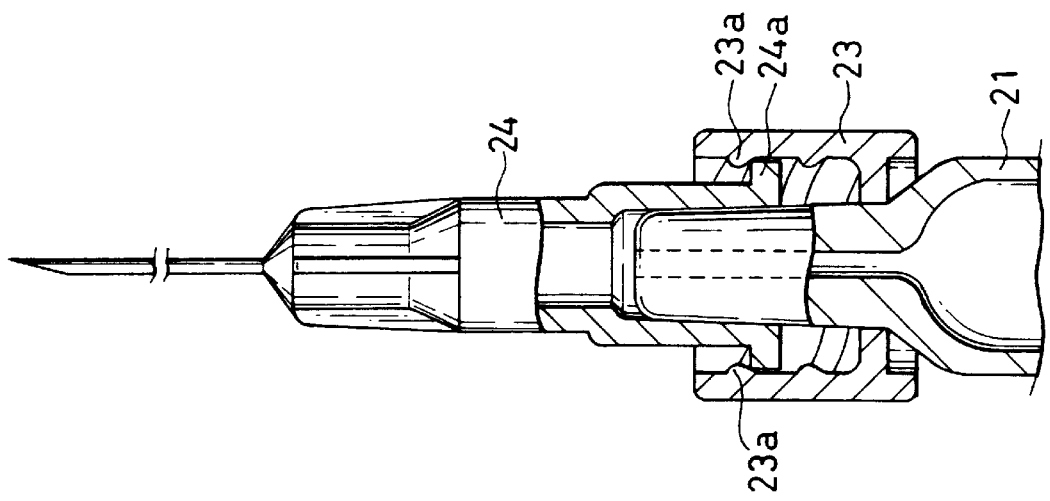

It is possible to make the spray adaptor 10 easily attachable to and removable from a syringe 20 which is designed to be fitted with a needle 24 by employing a differently shaped connector 12 as shown in FIGS. 8, 9A and 9B.

In this variation of the foregoing preferred embodiment, a socket 23 provided with internal threads 23a is mounted on the syringe 20 close to its discharge opening. The syringe 20 is readily loaded with collunarium and its discharge opening is closed by fitting a plug 25 (FIG. 9B). If the syringe 20 is to be used for direct injection of a liquid medicine-into a patient, the plug 25 is removed to expose the discharge opening of the syringe 20 and the needle 24 is screwed into the socket 23 (FIG. 9A). The internal threads 23a formed on a cylindrical inner surface of the socket 23 are double-start threads. The needle 24 has a flange 24a at its one end. The needle 24 can be properly mounted to the syringe 20 in alignment with its axis by engaging two peripheral parts of the flange 24a with the internal threads 23a of the socket 23 as shown in FIG. 9A.

Figure 10:
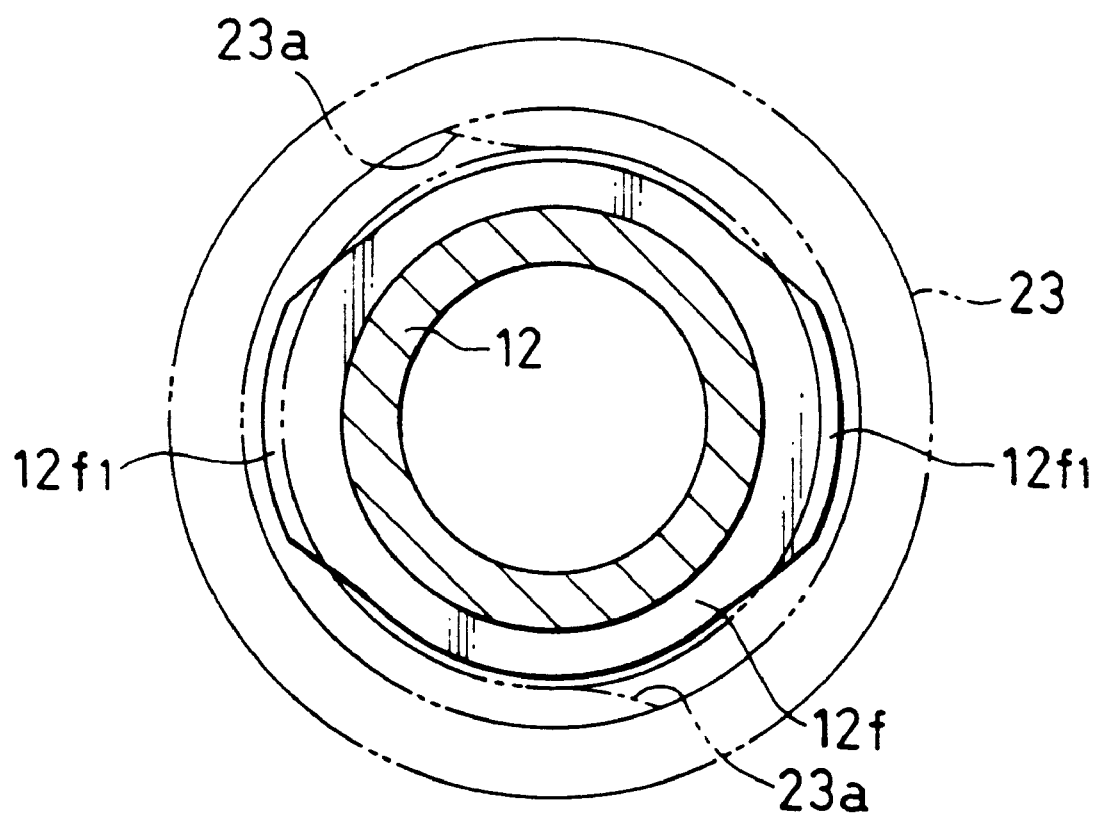
FIG. 10 is an enlarged horizontal sectional view taken along lines X—X of FIG. 8.

The connector 12 has at its lower end a flange 12f formed into the same shape and size as the flange 24a of the needle 24 (FIGS. 8 and 10). More particularly, the flange 12f has a pair of projecting parts $12f_1$ directed in opposite radial directions. The spray adaptor 10 is mounted to the upper end of the syringe 20 by screwing the projecting parts $12f_1$ of the flange 12f into the internal threads 23a of the socket 23 as shown in FIG. 8. The spray adaptor 10 can be easily removed from the syringe 20 after use by disengaging the projecting parts $12f_1$ from the internal threads 23a. The connector 12 has an upward-pointing nozzle portion 12e which is narrowed toward its upper end in a conical shape. The nozzle portion 12e is fitted into the vertical through hole $13c_1$ which passes through the receptacle 13c of the seal member 13. This nozzle portion 12e acts on the seal member 13 in the same fashion as the nozzle portion 21a of FIG. 4.

It will be appreciated from the above description that the syringe 20 of this variation can be used for injecting a liquid medicine when fitted with the needle 24 and for spraying the collunarium when fitted with the spray adaptor 10.

As described above, a spray adaptor of the invention comprises a connector adapted to be fitted to and removed from a liquid outlet of a syringe and a main adaptor element joined to the connector, the main adaptor element having a pair of spray nozzles suitably formed for simultaneous insertion into both nostrils.

The connector and the main adaptor element are joined together with a seal member placed between them. A part of the seal member acts as an on-off valve whose opening and closing operation is controlled by a flow of collunarium introduced from the syringe.

Further, a nozzle insertion hole is preferably formed in the connector for inserting a nozzle portion of the syringe. The spray adaptor is preferably made attachable to a syringe provided with a socket for fitting a needle. The connector is so constructed that it can be screwed into the socket.

The main adaptor element of the aforementioned spray adaptor has a pair of spray nozzles, and can be connected to a syringe preloaded with collunarium by using the connector.

With this arrangement, the collunarium can be into both nostrils at one time by operating the syringe with the spray nozzles inserted into the nostrils. This will reduce the time required for applying the collunarium, and simplify overall spraying operation.

The seal member sandwiched between the connector and the main adaptor element prevents the collunarium fed from the syringe from leaking to the outside of the spray adaptor. Preferably, the seal member is formed of a chemical-resistant elastic material, such as a rubber-based or synthetic-resin-based substance. The seal member employed in the spray adaptor has as its integral part an on-off valve which is activated by the collunarium fed from the syringe. When the pressure of the collunarium introduced from the syringe into a space between the main adaptor element and the connector reaches or exceeds a specified level, the on-off valve opens and allows the collunarium to flow into the spray nozzles of the main adaptor element. This arrangement serves to regulate the spray pressure of the spray nozzles to a constant level, and thereby stabilize the condition of atomization of the collunarium to be sprayed into the nostrils and control the amount of the collunarium applied to nasal mucous membranes to a constant level.

The connector having a nozzle insertion hole for inserting the nozzle portion of a syringe is adapted to a syringe having an elongated nozzle portion which can easily be inserted into a vial for sucking a liquid medicine into the syringe.

The connector capable of being screwed into the socket of a syringe is adapted to a syringe which is normally fitted with a needle. When removed from the connector of the spray adaptor, this type of syringe can be fitted with a needle and used for injecting a liquid medicine in an ordinary fashion.

Further, a sprayer of the invention comprises a syringe and a spray adaptor mounted to the syringe, in which the spray adaptor includes a connector detachably fitted to a liquid outlet of the syringe and a main adaptor element joined to the connector, the main adaptor element having a pair of spray nozzles suitably formed for simultaneous insertion into both nostrils.

The connector and the main adaptor element are preferably joined together with a seal member placed in between. A part of the seal member acts as an on-off valve whose opening and closing operation is controlled by a flow of of collunarium introduced from the syringe. The syringe to be used in the sprayer may be of a type readily loaded with the collunarium.

The sprayer can be easily prepared by joining together the syringe and the spray adaptor and used for spraying the collunarium into both nostrils at one time.

When using a syringe preloaded with the collunarium, it is not necessary to load the syringe with collunarium before spraying. This type of syringe may be preferably employ a glass barrel to prevent deterioration of its content and be provided with a socket for attaching a needle.

What is claimed is:

1. A spray adaptor for spraying collunarium comprising:
    a connector adapted to be fitted to and removed from a liquid outlet of a syringe; and
    a main adaptor element joined to said connector, said main adaptor element having pair of spray nozzles suitably formed for simultaneous insertion into both nostrils;
    said connector and said main adaptor element being joined together with a seal member placed in between and a part of said seal member acting as an on-off valve whose opening and closing operation is controlled by a flow of collunarium introduced from said syringe.

2. A spray adaptor for spraying collunarium according to claim 1 wherein said spray adaptor is made attachable to a syringe provided with a socket for fitting a needle, said connector being so constructed that it can be screwed into said socket.

3. A spray adaptor for spraying collunarium according to claim 1 wherein a nozzle insertion hole is formed in said connector for inserting a nozzle portion of said syringe.

4. A spray adaptor for spraying collunarium according to claim 1 wherein said spray adaptor is made attachable to a syringe provided with a socket for fitting a needle, said connector being so constructed that it can be screwed into said socket.

5. A sprayer for spraying collunarium comprising a syringe and a spray adaptor mounted to said syringe, said spray adaptor including:
    a connector detachably fitted to a liquid outlet of said syringe; and
    a main adaptor element joined to said connector, said main adaptor element having a pair of spray nozzles suitably formed for simultaneous insertion into both nostrils;
    said connector and said main adaptor element being joined together with a seal member placed in between and a part of said seal member acting as an on-off valve whose opening and closing operation is controlled by a flow of collunarium introduced from said syringe.

6. A sprayer for spraying collunarium according to claim 5 wherein said syringe is of a type readily loaded with the collunarium.

* * * * *